ative quantities of water, hydrogen, carbon dioxide and/or methane may be supplied to the process. In such cases, it is recommended to use the reactants in a molar ratio of carbon monoxide to hydrogen in the range from 1:1 to 10:1.

United States Patent [19]
Drent

[11] 4,356,126
[45] Oct. 26, 1982

[54] CARBONYLATION OF ALKANOLS AND/OR ALIPHATIC ETHERS

[75] Inventor: Eit Drent, Amsterdam, Netherlands

[73] Assignee: Shell Oil Company, Houston, Tex.

[21] Appl. No.: 274,616

[22] Filed: Jun. 17, 1981

[30] Foreign Application Priority Data

Jun. 19, 1980 [GB] United Kingdom ............... 8020045

[51] Int. Cl.³ .................. C07C 51/12; C07C 67/36; C07C 67/37; C07D 307/60
[52] U.S. Cl. .................. 260/410.9 R; 260/410.6; 260/413; 560/189; 560/198; 560/199; 560/200; 560/204; 560/232; 562/517; 562/519; 562/599; 568/671; 568/698; 568/899; 568/900; 549/233
[58] Field of Search ............... 560/189, 232, 204, 200, 560/106, 198–199, 114; 260/410.9 R, 410.6, 413, 346.74; 562/517, 519, 497

[56] References Cited

PUBLICATIONS

Webber et al., Journal of Catalysis 47, 269–271 (1977).

*Primary Examiner*—Vivian Garner

[57] ABSTRACT

Process for the carbonylation of alkanols and/or ethers at elevated temperature and pressure in the presence of a Group VIII metal compound and pentachlorobenzenethiol and/or salts thereof, using a pentachlorobenzenethiol compound: Group VIII metal compound molar ratio of not more than 10. The process is of special interest for the production of methyl acetate from methanol using an active, iodine-free catalytic system.

20 Claims, No Drawings

CARBONYLATION OF ALKANOLS AND/OR ALIPHATIC ETHERS

BACKGROUND OF THE INVENTION

1. Field of the Invention

This invention relates to a process for the carbonylation of alkanols and/or ethers using Group VIII metal catalysts and pentachlorobenzenethiol in a molar ratio of thiol: Group VIII metal compound of not more than 10.

2. Background

The present invention relates to a process for the carbonylation of alkanols and/or ethers under mild process conditions. The present invention relates in particular to the conversion of methanol into methyl acetate by a carbonylation process. Esters in general are valuable materials, either as such for use as solvents or plasticisers or as intermediates in the production of high value chemical compounds. Methyl acetate is a particularly versatile chemical; it can be used as starting material in a variety of chemical reactions.

It is known that methanol can be carbonylated using a rhodium-based catalyst and methyl iodide as a promotor to give methyl acetate and dimethyl ether as a by-product. The disadvantages connected with the use of iodine-containing systems are well known: not only do special precautions need to be taken to combat or prevent, as far as possible, corrosion but also the relatively high volatility of the iodine-compounds normally used (such as hydrogen iodine, methyl iodine or iodine itself) requires that several separations be applied in the recovery of the catalyst and promotor.

In order to overcome these drawbacks, the use of iodine-free catalytic systems based on pentachloro- and pentafluorobenzenethiol as promotor has been suggested (J. of Cat., 47, (1977) 269-277). It appears from this publication that methyl acetate can be produced, together with dimethyl ether, using a promotor: catalyst molar ratio of about 100:1. It is also mentioned that the effectiveness of the use of such promotors is rather low (about 4%) compared with the effectiveness of the use of methyl iodide as promotor under otherwise identical reaction conditions, and that to compensate for this low activity higher concentrations of promotor and higher temperatures could be applied. However, to increase the amount of promotor component (already used in amounts of more than 50% w calculated on methanol to be converted) would be very costly and moreover require severe working-up procedures.

It has now been found that the use of pentachlorobenzenethiol and/or salts thereof in very low pentachlorobenzenethiol compound: Catalyst molar ratios leads to the production of methyl acetate with high selectivity in yields comparable with those obtainable using methyl iodide in similar quantities.

SUMMARY OF THE INVENTION

The present invention relates to a process for the carbonylation of alkanols and/or ethers at elevated temperature and pressure in the presence of a Group VIII metal compound and pentachlorobenzenethiol and/or salts thereof which comprises using a pentachlorobenzenethiol compound: Group VIII metal compound molar ratio of not more than 10. The present invention relates in particular to the production of methyl acetate from methanol using pentachlorobenzenethiol: rhodium or iridium-metal compound molar ratio of not more than 10.

DESCRIPTION OF THE PREFERRED EMBODIMENTS

Alkanols which can be used conveniently as starting materials in the process according to the present invention comprise aliphatic alkanols having up to 12 carbon atoms. Mono-alkanols as well as poly-alkanols can be used. Examples of suitable mono-alkanols are methanol, ethanol, propanol, isopropanol, butanol, sec-butanol, t-butanol and also higher alkanols such as the hexanols and the actanols. Examples of suitable poly-alkanols are ethylene glycol, glycerol and butanediol-1,4. Preference is given to the use of lower alkanols having up to 6 carbon atoms such as methanol, ethanol and isopropanol, and especially to methanol. When using poly-alkanols such as ethylene glycol, a mixture of carbonylated products will normally be obtained. The alkanols to be used as starting materials need not be extremely pure; good results can be obtained using alkanols of normal commercial quality. Mixtures of alkanols can also be used.

It is also possible to use ethers as starting materials for the carbonylation according to the present invention. Ethers which can be used suitably comprise aliphatic mono-ethers having up to 20 carbon atoms. Examples of suitable ethers comprise methoxymethane, ethoxymethane, ethoxyethane, ethylene oxide and derivatives thereof as well as higher ethers such as the methoxybutanes. The use of ethers having different alkyl groups will normally lead to the production of mixtures of esters. Mixtures of ethers as well as mixtures of alkanols and ethers can also be used.

The catalytic systems to be used in the process according to the present invention comprise a Group VIII metal compound and pentachlorobenzenethiol and/or salts thereof wherein the molar ratio of pentachlorobenzenethiol compound: Group VIII metal compound is not more than 10 and preferably not more than 5. Typically the ratio ranges between about 1 to about 10, preferably between about 2 to about 5. It is remarkable that it is not an increase in the amount of promotor compounds as suggested in the publication referred to hereinbefore, but a very significant decrease in the amount of only one specific type of promotor which leads to an improved performance. It will be clear from Comparative Example C that the use of the closely related compound pentafluorobenzenethiol in catalytic amounts (calculated on Group VIII metal compound intake) almost completely destroys the activity as well as the selectivity of the carbonylation process.

Special reference is made to Group VIII metal compounds which contain rhodium or iridium. Suitable rhodium and iridium compounds comprise the chlorides and bromides, especially rhodium trichloride trihydrate and iridium trichloride, as well as rhodium and iridium coordination compounds according to the general formula $M(CO)_n(L)_m Hal_p$ wherein M represents a rhodium or iridium moiety; L an organic ligand such as an amine, an organo-phosphine, organo-arsine and/or organo-stibine ligand, an olefinically unsaturated ligand or an acetylacetone moiety; Hal represents a chlorine or bromine moiety; n and m are integers of from 0 to 3 and p is 0, 1 or 2, wherein n, m and p together satisfy the oxidation number and the coordination number of the moiety M.

Examples of suitable coordination or complex compounds according to the general formula $M(CO)_nL_mHal_p$ comprise compounds having the formula $M(CO)L_2Hal$ wherein L represents an organo-phosphine, an organo-arsine or organo-stibine moiety such as a trialkyl or triaryl or mixed alkyl/aryl phosphine, arsine or stibine; and Hal represents a chlorine or bromine moiety, for example the compound $Ir(CO)(P(C_6H_5)_3)_2Cl$ and the corresponding rhodium compound and similar compounds known to those skilled in the art. Another group of suitable compounds comprises compounds according to the general formula $ML_3Hal$, such as $Rh(P(nC_4H_9)_3)_3Cl$ or $RH(P(C_6H_5)_3)_3Br$ and the corresponding iridium compounds. Good results have been obtained using compounds wherein L represents an acetylacetone moiety, as for instance in the complex $Rh(acac)(CO)_2$ wherein acac represents an acetylacetonyl group. An example of a compound containing an olefinically unsaturated ligand is $(1,5-COD)IrCl_2$, wherein 1,5-COD represents the 1,5-cyclooctadienyl group. If desired, additional amounts of ligands of formula L can be added to the complex and/or the reaction mixture. For instance, an excess of triphenyl phosphine or α-picoline can be suitably used.

The Group VIII metal compounds can be employed within very wide weight ranges. Normally, amounts as low as 0.001% w (calculated on compound(s) to be carbonylated) can be used in the catalytic carbonylation according to the present invention. Preference is given to Group VIII metal compounds in the range of from about 0.01% w to about 5% w, calculated on compound(s) to be carbonylated.

Apart from pentachlorobenzenethiol itself, also salts of pentachlorobenzenethiol can be used in the process according to the present invention, either as such or in combination with each other and/or with pentachlorobenzenethiol. Suitable salts comprise Group I, II and III metal salts such as lithium pentachlorobenzenethiolate, sodium pentachlorobenzenethiolate, potassium pentachlorobenzenethiolate, magnesium di(pentachlorobenzenethiolate), calcium di(pentachlorobenzenethiolate), zinc di(pentachlorobenzenethiolate) and aluminium tri (pentachlorobenzenethiolate). Preference is given to the use of pentachlorobenzenethiol and/or Group I[a] and Group II[b] metal salts thereof, in particular lithium pentachlorobenzenethiolate and zinc di(pentachlorobenzenethiolate).

It is also possible to use pentachlorobenzenethiol anchored to a polymer backbone in the process according to the present invention. Chloromethylated polystyrenes, optionally containing small amounts of crosslinking agents such as divinylbenzene, are good starting materials for preparing anchored pentachlorobenzenethiol by methods described in the art.

As mentioned hereinbefore, the amount of pentachlorobenzenethiol and/or salt(s) thereof is rather critical with respect to the selectivity of the carbonylation process. It has been found (comparative Example A) that when a pentachlorobenzenethiol: Group VIII metal compound molar ratio of about 15 is applied in the carbonylation of methanol, the main product is dimethyl ether rather than methyl acetate. Good results can be obtained using a molar ratio of not more than about 10, preferably not more than about 5. Very good results have been obtained using a pentachlorobenzenethiol compound: Group VIII metal compound ratio between 2 and 5.

The process according to the present invention is normally carried out at elevated temperature and pressure. Temperatures of up to 300° C. can be suitably applied. Preference is given to temperatures in the range of from about 100° C. to about 225° C.; most preferred temperatures are in the range of from about 125° C. to about 200° C. The process can be carried out using low carbon monoxide pressures, e.g. pressures as low as 5 bar. Pressures in the range of from about 20 to about 100 bar are preferred. Higher pressures can also be used but they do not contribute substantially. It has been found that optional results can be achieved using a moderate initial pressure; for instance initial carbon monoxide pressures of from about 20–50 bar. It has also been found that the presence of hydrogen can be tolerated in rather large quantities, e.g. quantities of up to about 50% on a molar basis calculated on carbon monoxide.

The reaction time is not critical and will depend largely on the temperature and pressure applied. Reaction times of from about 1 to about 30 hours are sufficient, preference being given to reaction times in the range of from about 2 to about 15 hours.

The process according to the present invention can be carried out in the presence or in the absence of a solvent. It will be understood that the alkanol and/or ether to be carbonylated may be considered themselves as solvents.

It has been found that sulphur-containing solvents can be used with very good results in the process according to the present invention. Suitable sulphur-containing solvents comprise cyclic as well as acyclic sulphones and sulphoxides. They can be represented by the general formula

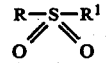

wherein R and R[1] represent the same or different aliphatic groups which may be joined together to form a cyclic sulphone. Suitable acyclic sulphones are those according to the above formula wherein R and R[1] represent the same or different alkyl groups such as $C_1$ to about $C_{12}$ alkyl groups. Specific examples include dimethyl, diethyl, dipropyl, methylethyl and methylbutylsulphones. Preferred cyclic sulphones are sulpholane and alkylsulpholanes, such as those sulpholanes substituted by one or more $C_1$ to about $C_8$ alkyl groups. Specific examples include 2-methylsulpholane, 3-methylsulpholane, 3-butylsulpholane, 3-isopropylsulpholane and 2-methyl-3-butylsulpholane. Preference is given to the use of sulpholane as a solvent as this solvent combines the attractive combination of high activity and high selectivity of the carbonylations carried out therein. Suitable sulphoxides may be represented by the general formula

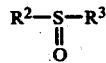

wherein R[2] and R[3] which may be the same or different represent alkyl groups of up to about 12 carbon atoms. Specific examples include dimethylsulphoxide and diethylsulphoxide.

The amount of solvent which may be applied in the process according to the present invention may vary between wide limits. Volumes of solvent as high as about 50 times the volume of the reagent(s) can be suitably applied. Normally amounts of solvent up to about 2 to about 5 times the amount of reactant(s) will be used. It has been found that rather small amounts of sulphur-containing compounds as described hereinabove, e.g. in amounts as low as about 10% v on reactant(s) can also be used suitably.

The process according to the present invention can be carried out in the liquid phase as well as in the gaseous phase. Preference is given to a liquid phase which enables a convenient introduction of carbon monoxide into the reaction vessel. The process according to the present invention can be carried out batchwise, semi-continuously or continuously. The reaction can be suitably carried out in one or more autoclaves, or one or more reactor tubes whose walls are preferably made of or coated with inert materials.

The process according to the present invention may be integrated with processes which either produce the starting alkanol and/or ether or use the ester and/or acid produced as a starting material for a further chemical reactive. For instance, methyl acetate produced by the carbonylation of methanol using the process according to the present invention can be used advantageously as a starting material in the production of acetic anhydride by methods known in the art.

It is also possible to integrate a process for the carbonylation of alkanols according to the present invention with a process for the hydration of olefins giving the starting alkanol, e.g. the carbonylation of isopropanol according to the present invention can be integrated with a process for the hydration of propylene giving isopropanol. It has been found, for instance that propylene can be present during the carbonylation of isopropanol which means that the product stream from the propylene hydration reaction can be directly used as feedstock for the carbonylation process according to the present invention and that propylene and/or isopropanol present in the final product(s) can be partly or totally recycled after the separation to earlier stages in the integrated process.

The reaction mixture may be worked up by techniques known in the art. For instance, the reaction mixture may be subjected to a (fractional) distillation to separate the starting material, the solvent, if any and the ester(s) and/or acid(s) produced. If desired further purification treatment can be given to the product(s) obtained.

The invention will now be illustrated by means of the following non-limiting Examples.

EXAMPLE I

The experiment was carried out in a 250 ml magnet-driven autoclave of Hastelloy B which contained methanol (50 ml), 1 mmol rhodium (III) chloride trihydrate and 3 mmol pentachlorobenzenethiol. The vessel was flushed with carbon monoxide and further charged with carbon monoxide to a pressure of 50 bar. The autoclave was then heated to 175° C. and kept at this temperature for 15 hours. After cooling, the contents of the reactor was analyzed using gas-liquid chromatography. Calculated on a molar basis the conversion of the starting material methanol was 14% with a product selectivity (expressed on a weight basis) towards methyl acetate of 68% and to dimethyl ether of 32%.

COMPARATIVE EXAMPLE A

The experiment described in the previous Example was repeated using the same amount of methanol and rhodium (III) chloride trihydrate but 5 times the amount of pentachlorobenzenethiol, thus using a pentachlorobenzenethiol: Group VIII metal compound ratio of 15:1. After 15 hours reaction at 175° C., the conversion of methanol appeared to be 16%. The main product was dimethylether (63%). The desired product methyl acetate had only been found in an amount of 20%, the remainder being unidentified products. It will be clear friom this Comparative Example that the amount of pentachlorobenzenethiol to be used is very critical with respect to the selectivity of the reaction.

EXAMPLE II

The experiment as described in Example I was repeated using an initial carbon monoxide pressure of 30 bar. From gas-liquid chromatography it appeared that the conversion of methanol amounted to 40% and that the selectivity towards methyl acetate was 75%, the remainder being dimethylether. The ester production rate, calculated as g ester produced/g rhodium (III)/g pentachlorobenzenethiol/hour was about 4 times higher than that found for the experiment described in Example I, which was already about 18 times higher than that found for the experiment described in Comparative Example A.

EXAMPLE III

The experiment as described in Example II was repeated using isopropanol (50 ml) as the compound to be carbonylated, and a pentachlorobenzenethiol: rhodium (III) chloride trihydrate ratio of 4:1 (in mmol). The conversion of isopropanol into butyrates amounted to 15%, the selectivity of the carbonylation expressed as $$\frac{iso}{iso + normal}$$

was 94%. No butyric acids could be detected. It should be noted that the carbonylation of isopropanol proceeds with a very high selectivity towards isopropyl isobutyrate.

EXAMPLE IV

The experiment described in Example II was repeated using methanol (10 ml) and sulpholane (30 ml) as the solvent. The initial carbon monoxide pressure amounted to 30 bar. After 15 hours at 175° C., the reaction mixture was cooled and analysed. The conversion of methanol was virtually complete and the selectivity towards methyl acetate was 92%, the remainder being dimethyl ether (8%). The ester production rate was even higher than that found in the experiment described in Example II.

EXAMPLE V

The experiment described in Example IV was repeated using rhodium (III) chloride trihydrate (0.5 mmol) and zinc di(pentachlorobenzenethiolate) (1.5 mmol) instead of pentachlorobenzenethiol under otherwise similar reaction conditions. The conversion of methanol amounted to 80%. The selectivity towards methyl acetate was 83%, the remainder being dimethylether (10%) and acetic acid (7%).

Example VI

The experiment described in Example IV was repeated using the same pentachlorobenzenethiol: Group VIII metal compound ratio, but only half of the amounts used in the experiment described in Example IV. The conversion of methanol amounted under otherwise similar conditions to 96%. The selectivity towards methyl acetate was 86% and the remainder (14%) was again dimethylether. It was found that under these circumstances the ester production rate (g ester produced /g rhodium (III) /g pentachlorobenzenethiol/hour) was over three times higher than that found in the experiment described in Example II. The Examples IV and VI duly illustrate the advantages of using sulpholane as the solvent in the carbonylation of methanol according to the present invention.

EXAMPLE VII

The experiment described in Example IV was repeated using a pentachlorobenzenethiol: rhodium (III) chloride trihydrate ratio of 3.7 (in mmol). The reaction was carried out for 2 hours at 175° C. after an initial activation of 3 hours at 180° C. (no visible reaction observed). The conversion of methanol amounted to 59%. The selectivity towards methyl acetate was 84%, the remainder being dimethylether.

EXAMPLE VIII

The experiment described in Example IV was repeated but using methylbutylether as the compound to be carbonylated. From the gas-liquid chromatography it appeared that the main product was butyl acetate; a trace of methyl pentanoate had also been formed.

EXAMPLE IX

The experiment described in Example IV was carried out using isopropanol (10 ml) and sulpholane (30 ml) as the solvent. Under these conditions butyric acids had been formed with a selectivity, expressed as $$\frac{iso}{iso + normal}$$

of 62%. The conversion of the starting material amounted to 98%. When the experiment was repeated during a shorter reaction time (5 hours the conversion was 92% and the selectivity as expressed hereinbefore amounted to 65%.

EXAMPLE X

The experiment described in Example IX was repeated using isopropanol as the feedstock in the presence of propylene (initial pressure 6 bar) whilst the carbon monoxide initial pressure amounted to 24 bar. The conversion of isopropanol was 80% and isopropyl isobutyrate: isopropyl n-butyrate ratio found (i/n) was 1.5.

EXAMPLE XI

The experiment described in the previous Example was repeated using half the amount of rhodium (III) chloride trihydrate and pentachlorobenzenethiol in the presence of free triphenylphosphine (3 mmol). After 15 hours at 175° C., the conversion of isopropanol amounted to 70% whereas the i/n product ratio was 1.7. When this experiment was repeated using the iridium compound IrCl(CO)(P(C₆H₅)₃)₂ as the Group VIII metal compound, the conversion amounted to 70% and the i/n product ratio was 0.4.

EXAMPLE XII

The experiment described in Example IX was repeated using isopropanol (40 ml) as the compound to be carbonylated in the presence of a small amount sulpholane (5 ml). Under otherwise identical conditions, the conversion of isopropanol into butyrates amounted to 30% and the selectivity expressed as $$\frac{iso}{iso + normal}$$

was 90%. A small amount of butyric acids had also been formed (up to about 10%).

COMPARATIVE EXAMPLE B

The experiment described in Example III was repeated using 4 mmol of methyl iodide instead of pentachlorobenzenethiol. Although the conversion amounted to 46%, the selectivity, expressed as $$\frac{iso}{iso + normal}$$

was rather poor (46%). Also some butyric acids had been formed.

EXAMPLE XIII

The experiment described in Example IV was repeated using Rh(acac)(CO)₂(0.5 mmol) as the Group VIII metal compound. The conversion of methanol amounted to 92%. The selectivity towards methyl acetate was 82% and the remainder (18%) was dimethylether.

EXAMPLE XIV

The experiment described in the previous Example was repeated using as the Group VIII metal compound IrCl(P(C₆H₅)₃)₂CO. The conversion of methanol amounted to 95%. The selectivity towards methyl acetate was 90%, the remainder being dimethylether.

EXAMPLE XV

The experiment described in Example VI was repeated using rhodium (III) chloride trihydrate as the Group VIII metal compound together with 1 mmmol of triphenyl phosphine. The conversion of methanol amounted to 94%. The selectivity towards methyl acetate was 88%, the remainder being dimethylether.

EXAMPLE XVI

The experiment described in the previous Example was repeated but using 1 mmol of α-picoline instead of triphenyl phosphine. The conversion of methanol amounted to 50%. The selectivity towards methyl acetate was 89%, the remainder being dimethyl ether.

COMPARATIVE EXAMPLE C

The experiment described in Example VI was repeated but using pentafluorobenzenethiol instead of pentachlorobenzenethiol. The conversion of methanol was less than 5% and the selectivity towards methyl acetate was also less than 5%. Also some decomposition of the thiol was observed. It will be clear from this Comparative Example that the use of pentafluorobenzenethiol, even in a low pentafluorobenzenethiol:

Group VIII metal compound ratio does not give any acceptable result at all.

COMPARATIVE EXAMPLE D

The experiment described in the previous Comparative Example was repeated but using 4-chlorobenzenethiol instead of pentafluorobenzenethiol. Again the conversion of methanol was extremely low (<5%) and the selectivity towards methyl acetate was less than 5%.

COMPARATIVE EXAMPLE E

The experiment described in the previous Comparative Example was repeated but using perchlorocyclopentadiene instead of p-chlorobenzenethiol. In order to activate the co-catalyst, hydrogen (initial pressure 5 bar) was also present. The conversion of methanol was rather poor (<10%) and the selectivity towards methyl acetate again less than 5%.

EXAMPLE XVII

The experiment described in Example IV was repeated using a 1,2-dihydroxyethane-water mixture (10 ml/10 ml) instead of methanol. From gas-liquid chromatography it appeared that the following compounds had been formed: hydroxybutyric acid, succinic acid (anhydride), acrylic acid and propionic acid.

EXAMPLE XVIII

The carbonylation of methanol was carried out using the catalytic system described in Example II. Prior to the reaction the catalytic system was activated in carbon monoxide at 180° C. during 2 hours. Thereafter the temperature was lowered to 150° C. and the reaction was performed in the presence of hydrogen (molar ratio carbon monoxide: hydrogen 1:1). After 13 hours at 150° C. it appeared from gas-liquid chromatography that the conversion of methanol amounted to 60%; the selectivity towards methyl acetate was 74%, the remainder being dimethylether. The experiment described hereinbefore was repeated in the absence of hydrogen. The conversion amounted to 40% and the selectivity towards methyl acetate was 63%, the remainder being dimethyl ether. This Example clearly demonstrates that hydrogen can be tolerated during the carbonylation of methanol according to the process according to the present invention.

Claim:

1. A process for the carbonylation of alkanols and/or aliphatic ethers at a temperature of about 100° C.–225° C. and a pressure of about 20–100 bar in the presence of a Group VIII metal compound and pentachlorobenzenethiol and/or salts thereof, which comprises reacting the alkanols or aliphatic ethers with carbon monoxide using a pentachlorobenzenethiol compound: Group VIII metal compound molar ratio of not more than about 10.

2. The process according to claim 1, which comprises using a pentachlorobenzenethiol compound: Group VIII metal compound molar ratio of not more than about 5.

3. The process according to claim 2, which comprises using a pentachlorobenzenethiol compound: Group VIII metal compound molar ratio between about 2 and about 5.

4. The process according to claim 1, which comprises using pentachlorobenzenethiol and/or a Group I, II or III metal salt thereof.

5. The process according to claim 4, which comprises using pentachlorobenzenethiol and/or a Group $I^a$ or $II^b$ metal salt thereof.

6. The process according to claim 5, which comprises using pentachlorobenzenethiol and/or zinc di(pentachlorobenzenethiolate).

7. The process according to claim 1, which comprises using as starting material an alkanol having up to about twelve carbon atoms.

8. The process according to claim 7, which comprises using as starting material is lower alkanol having up to about six carbon atoms.

9. The process according to claim 8, which comprises using as starting material methanol.

10. The process according to claim 1, which comprises using as starting material an aliphatic monoether having up to about twenty carbon atoms.

11. The process according to claim 1, which comprises using as Group VIII metal compound a rhodium or an iridium compound.

12. The process according to claim 11, which comprises using rhodium (III) chloride trihydrate or a compound according to the general formula $M(CO)_nL_mHal_p$ wherein M represents a rhodium or iridium moiety; L an organic ligand selected from the group of an amine, an organo-phosphine, organo-arsine and/or organo-stibine ligand, an olefinically unsaturated ligand or an acetylacetone moiety; Hal represents a chlorine or bromine moiety; and m and n are integers of from 0 to 3 and p it 0, 1 or 2, wherein n, m and p together satisfy the oxidation number and the coordination number of the moiety M.

13. The process according to claim 12, which comprises using a compound according to the general formula $M(CO)L_2Hal$ or $ML_3Hal$.

14. The process according to claim 11, which comprises using the Group VIII metal compound in an amount in the range of from 0.01% w to 5% w, calculated on compound(s) to be carbonylated.

15. The process according to claim 1, which comprises performing the reaction in the presence of hydrogen.

16. The process according to claim 1, which comprises performing the reaction in the presence of a sulphur-containing solvent.

17. The process according to claim 16, which comprises performing the reaction in the presnece of a cyclic or acyclic sulphone or a sulphoxide.

18. The process according to claim 17, which comprises performing the reaction in the presence of sulpholane.

19. The process according to claim 17, which comprises using the solvent in an amount up to about 5 times the amount of reactant(s).

20. The process according to claim 19, which comprises using the solvent in an amount up to about 2 times the amount of reactant(s).

* * * * *